US011103587B2

(12) United States Patent
Weeden et al.

(10) Patent No.: US 11,103,587 B2
(45) Date of Patent: Aug. 31, 2021

(54) MULTIPLE OLIGONUCLEOTIDE MOIETIES ON PEPTIDE CARRIER

(71) Applicant: Genzyme Corporation, Cambridge, MA (US)

(72) Inventors: Timothy E. Weeden, Sturbridge, NJ (US); Carol A. Nelson, Westford, MA (US); Bruce M. Wentworth, Northborough, MA (US); Nicholas P. Clayton, Sudbury, MA (US); Andrew Leger, Boston, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 16/265,883

(22) Filed: Feb. 1, 2019

(65) Prior Publication Data

US 2019/0388547 A1 Dec. 26, 2019

Related U.S. Application Data

(63) Continuation of application No. 15/313,405, filed as application No. PCT/US2015/032142 on May 22, 2015, now abandoned.

(60) Provisional application No. 62/002,296, filed on May 23, 2014.

(51) Int. Cl.
*A61K 47/54* (2017.01)
*C12N 15/11* (2006.01)

(52) U.S. Cl.
CPC .......... *A61K 47/549* (2017.08); *C12N 15/111* (2013.01); *C12N 2310/11* (2013.01); *C12N 2310/3145* (2013.01); *C12N 2310/3233* (2013.01); *C12N 2310/3513* (2013.01); *C12N 2320/32* (2013.01)

(58) Field of Classification Search
CPC .................................................... A61K 47/549
See application file for complete search history.

(56) References Cited

U.S. PATENT DOCUMENTS

| 8,420,396 | B2 | 4/2013 | Uhlmann et al. |
| 2004/0265879 | A1 | 12/2004 | Iversen et al. |
| 2009/0082547 | A1 | 3/2009 | Iversen et al. |
| 2010/0130591 | A1 | 5/2010 | Sazani et al. |
| 2017/0182171 | A1 | 6/2017 | Weeden et al. |

FOREIGN PATENT DOCUMENTS

| RU | 2275936 C2 | 5/2006 |
| WO | WO-1995/006056 A1 | 3/1995 |
| WO | WO-2004/097017 A2 | 11/2004 |
| WO | WO-2009/005793 A2 | 1/2009 |
| WO | WO-2009/144481 A2 | 12/2009 |
| WO | WO-2009/147368 A1 | 12/2009 |
| WO | WO-2012/177639 A2 | 12/2012 |
| WO | WO-2013/040429 A1 | 3/2013 |
| WO | WO-2014/052276 A1 | 4/2014 |
| WO | WO-2015/113922 A1 | 8/2015 |

OTHER PUBLICATIONS

Amantana, A. et al. (2007; e-pub. Jun. 21, 2007). "Pharmacokinetics, Biodistribution, Stability and Toxicity of a Cell-Penetrating Peptide-Morpholino Oligomer Conjugate," *Bioconjugate Chem.* 18(4):1325-1331.
Frankel, A.D. et al. (Dec. 23, 1988). "Cellular Uptake of the Tat Protein From Human Immunodeficiency Virus," *Cell* 55(6):1189-1193.
Frankel, A.D. et al. (Jun. 3, 1988). "Fingering Too Many Proteins," *Cell* 53(5):675.
Green, M. et al. (Dec. 23, 1988). "Autonomous Functional Domains of Chemically Synthesized Human Immunodeficiency Virus Tat Trans-Activator Protein," *Cell* 55(6):1179-1188.
Green, M. et al. (Jun. 17, 1988). "An Adenovirus E1A Protein Domain Activates Transcription In Vivo and In Vitro in the Absence of Protein Synthesis," *Cell* 53(6):921-926.
International Preliminary Report on Patentability dated Dec. 8, 2016 for PCT Application No. PCT/US2015/032142 filed on May 22, 2015, 8 pages.
International Search Report dated Sep. 16, 2015 for PCT Application No. PCT/US2015/032142 filed on May 22, 2015, 5 pages.
Järver, P. et al. (Jun. 2012; e-pub. Jun. 12, 2012). "Peptide-mediated Cell and In Vivo Delivery of Antisense Oligonucleotides and siRNA," *Molecular Therapy—Nucleic Acids* 1(6):e27.
Jearawiriyapaisarn, N. et al. (Sep. 2008). "Sustained Dystrophin Expression Induced by Peptide-Conjugated Morpholino Oligomers in the Muscles of mdx Mice," *Molecular Therapy* 16(9):1624-1629.
Moulton, H.M. et al. (2010; e-pub. Feb. 17, 2010). "Morpholinos and their Peptide Conjugates: Therapeutic Promise and Challenge for Duchenne Muscular Dystrophy," *Biochima et Biophysica Acta* 1798:2296-2303.
Pierce, T.L. et al. (2005). "Peptide-Oligonucleotide Hybrids in Antisense Therapy," *Mini-Reviews in Medicinal Chemistry* 5(1):41-55.
Written Opinion dated Sep. 16, 2015 for PCT Application No. PCT/US2015/032142 filed on May 22, 2015, 6 pages.

*Primary Examiner* — Joseph R Kosack
(74) *Attorney, Agent, or Firm* — Morrison & Foerster LLP

(57) ABSTRACT

The present disclosure relates to antisense oligonucleotides (AONs), such as phosphorodiamidate morpholino oligonucleotides (PMOs). The present disclosure further relates to the conjugation of multiple PMOs to cationic cell penetrating peptides (CPPs) to enhance the uptake of PMOs into skeletal and cardiac muscle cells.

14 Claims, 3 Drawing Sheets
Specification includes a Sequence Listing.

FIG. 1

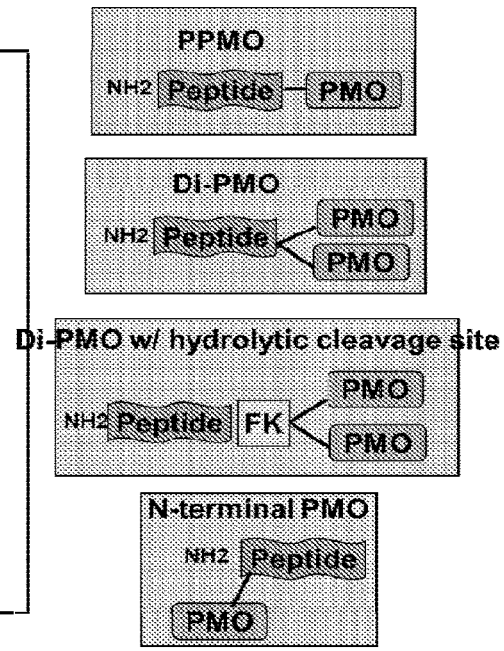

K series
Ac-(RXR)4 XA-PMO  - PPMO-K
Ac-(RXR)4 XEG-(PMO)2 – PPMO-Di-K
Ac-(RXR)4 FKEG-(PMO)2 – PPMO-Di-K + "FK" cathepsin site B series
Ac-(RXRRBR)2XBA-PMO  - PPMO-B
E(PMO)(RXRRBR)2XFKG- n-terminal PPMOB
Ac-(RXRRBR)2XEG-(PMO)2 – Di-PMO-B
Ac-(RXRRBR)2FKEG-(PMO)2 -Di-PMO-K with cathepsin site X = aminohexanoic acid
E = glutamic acid
FK = cathepsin site
B= beta-alanine K series SEQ ID NOS from top to bottom

SEQ ID NO.: 92

SEQ ID NO.: 93

SEQ ID NO.: 94

B series SEQ ID NOS from top to bottom

SEQ ID NO.: 82

SEQ ID NO.: 89

SEQ ID NO.: 90

SEQ ID NO.: 91

SEQUENCE LISTING

```
<160> NUMBER OF SEQ ID NOS: 96

<210> SEQ ID NO 1
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 1

Arg Xaa Xaa Xaa Xaa Xaa Arg Arg Arg Xaa Phe Ser Gln Gly
1               5                   10

<210> SEQ ID NO 2
```

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 2

Arg Xaa Xaa Xaa Xaa Xaa Xaa Arg Arg Xaa Phe Ser Gln Gly
1               5                   10

<210> SEQ ID NO 3
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 3

Arg Xaa Xaa Xaa Arg Xaa Arg Xaa Arg Xaa Phe Ser Gln Gly
1               5                   10
```

```
<210> SEQ ID NO 4
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: cis-2-aminocyclopentane-1-carbonyl
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 4

Arg Arg Xaa Xaa Xaa Xaa Xaa Xaa Arg Xaa Phe Ser Gln Gly
1               5                   10

<210> SEQ ID NO 5
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 5
```

Arg Arg Arg Xaa Xaa Xaa Xaa Xaa Arg Xaa Phe Ser Gln Gly
1               5                   10

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 6

Arg Xaa Arg Xaa Xaa Xaa Xaa Xaa Arg Xaa Phe Ser Gln Gly
1               5                   10

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)

```
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 7

Arg Arg Xaa Xaa Xaa Xaa Xaa Xaa Arg Xaa Phe Ser Gln Gly
1               5                   10

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: cis-2-aminocyclopentane-1-carbonyl
<220> FEATURE:
<221> NAME/KEY: MOD_RES
<222> LOCATION: (10)..(10)
<223> OTHER INFORMATION: 6-aminohexanoic acid

<400> SEQUENCE: 8

Arg Xaa Xaa Xaa Xaa Xaa Xaa Xaa Arg Xaa Phe Ser Gln Gly
1               5                   10

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: cis-2-aminocyclopentane-1-carbonyl
```

```
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 9

Arg Xaa Xaa Xaa Xaa Arg Xaa Xaa Arg Xaa Phe Ser Gln Gly
1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 10

Arg Arg Xaa Arg Xaa Xaa Xaa Xaa Arg Xaa Phe Ser Gln Gly
1               5                   10

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
<220> FEATURE:
```

```
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 11

Arg Arg Xaa Xaa Xaa Xaa Xaa Xaa Arg Xaa Phe Ser Gln Gly
1               5                   10

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 12

Arg Xaa Xaa Xaa Xaa Xaa Arg Xaa Arg Xaa
1               5                   10

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (2)..(2)
<223> OTHER INFORMATION: cis-2-aminocyclopentane-1-carbonyl
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 13

Arg Xaa Xaa Xaa Xaa Xaa Arg Xaa Arg Xaa
1               5                   10

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 14

Arg Xaa Xaa Xaa Xaa Xaa Arg Xaa Arg Xaa
1               5                   10

<210> SEQ ID NO 15
<211> LENGTH: 10
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: 6-aminohexanoic acid

<400> SEQUENCE: 15

Arg Arg Arg Arg Arg Arg Arg Arg Arg Xaa
1               5                   10

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 16

Arg Xaa Arg Xaa Xaa Xaa Xaa Xaa Arg Xaa
1               5                   10

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
```

```
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 17

Arg Xaa Xaa Xaa Xaa Xaa Xaa Xaa Arg Xaa
1               5                   10

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 18

Arg Arg Arg Xaa Xaa Xaa Xaa Xaa Arg Xaa
1               5                   10

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
```

```
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 19

Arg Xaa Xaa Xaa Xaa Xaa Arg Arg Arg Xaa
1               5                   10

<210> SEQ ID NO 20
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 20

Arg Xaa Xaa Xaa Xaa Xaa Xaa Arg Arg Xaa
1               5                   10

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 21

Arg Xaa Xaa Xaa Xaa Arg Xaa Xaa Arg Xaa
1               5                   10

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 22

Arg Xaa Xaa Xaa Arg Xaa Arg Xaa Arg Xaa
1               5                   10

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                                   Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 23

Arg Xaa Arg Xaa Xaa Xaa Xaa Xaa Arg Xaa
1               5                   10

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: cis-2-aminocyclopentane-1-carbonyl
<220> FEATURE:
<221> NAME/KEY: MOD_RES
<222> LOCATION: (10)..(10)
<223> OTHER INFORMATION: 6-aminohexanoic acid

<400> SEQUENCE: 24
```

Arg Xaa Xaa Xaa Xaa Xaa Xaa Xaa Arg Xaa
1               5                   10

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: cis-2-aminocyclopentane-1-carbonyl
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: cis-2-aminocyclopentane-1-carbonyl
<220> FEATURE:
<221> NAME/KEY: MOD_RES
<222> LOCATION: (10)..(10)
<223> OTHER INFORMATION: 6-aminohexanoic acid

<400> SEQUENCE: 25

Arg Xaa Xaa Xaa Xaa Xaa Xaa Xaa Arg Xaa
1               5                   10

<210> SEQ ID NO 26
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane

```
<220> FEATURE:
<221> NAME/KEY: MOD_RES
<222> LOCATION: (10)..(10)
<223> OTHER INFORMATION: 6-aminohexanoic acid

<400> SEQUENCE: 26

Arg Xaa Xaa Xaa Arg Xaa Xaa Arg Arg Xaa
1               5                   10

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 27

Arg Arg Xaa Xaa Xaa Xaa Arg Xaa Arg Xaa
1               5                   10

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: cis-2-aminocyclopentane-1-carbonyl
<220> FEATURE:
<221> NAME/KEY: MOD_RES
<222> LOCATION: (6)..(6)
<223> OTHER INFORMATION: 3-cis-aminocyclohexane
<220> FEATURE:
```

-continued

```
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 28

Arg Xaa Xaa Xaa Xaa Xaa Xaa Arg Arg Xaa
1               5                   10

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: cis-2-aminocyclopentane-1-carbonyl
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 29

Arg Xaa Xaa Xaa Xaa Xaa Xaa Arg Arg Xaa
1               5                   10

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
```

```
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 30

Arg Arg Xaa Arg Xaa Xaa Xaa Xaa Arg Xaa
1               5                   10

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: cis-2-aminocyclopentane-1-carbonyl
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 31

Arg Xaa Xaa Xaa Xaa Xaa Xaa Xaa Arg Xaa
1               5                   10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
```

```
<223> OTHER INFORMATION: cis-2-aminocyclopentane-1-carbonyl
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 32

Arg Xaa Xaa Arg Xaa Xaa Xaa Xaa Arg Xaa
1               5                   10

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 33

Arg Xaa Xaa Xaa Xaa Xaa Xaa Xaa Arg Xaa
1               5                   10

<210> SEQ ID NO 34
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: cis-2-aminocyclopentane-1-carbonyl
<220> FEATURE:
<221> NAME/KEY: MOD_RES
<222> LOCATION: (5)..(5)
<223> OTHER INFORMATION: cis-2-aminocyclopentane-1-carbonyl
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 34

Arg Xaa Xaa Xaa Xaa Xaa Xaa Xaa Arg Xaa
1               5                   10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid
```

<400> SEQUENCE: 35

Arg Xaa Xaa Xaa Xaa Xaa Xaa Arg Arg Xaa
1               5                   10

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: cis-2-aminocyclopentane-1-carbonyl
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 36

Arg Xaa Xaa Xaa Xaa Xaa Xaa Xaa Arg Xaa
1               5                   10

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:

```
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 37

Arg Xaa Arg Xaa Xaa Arg Xaa Xaa Arg Xaa
1               5                   10

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: cis-2-aminocyclopentane-1-carbonyl
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: cis-2-aminocyclopentane-1-carbonyl
<220> FEATURE:
<221> NAME/KEY: MOD_RES
<222> LOCATION: (10)..(10)
<223> OTHER INFORMATION: 6-aminohexanoic acid

<400> SEQUENCE: 38

Arg Arg Xaa Xaa Xaa Xaa Xaa Xaa Arg Xaa
1               5                   10

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
```

```
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 39

Arg Xaa Xaa Xaa Xaa Xaa Xaa Xaa Arg Xaa
1               5                   10

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 40

Arg Arg Xaa Xaa Xaa Xaa Xaa Xaa Arg Xaa
1               5                   10

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
```

```
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: cis-2-aminocyclopentane-1-carbonyl
<220> FEATURE:
<221> NAME/KEY: MOD_RES
<222> LOCATION: (6)..(6)
<223> OTHER INFORMATION: 3-cis-aminocyclohexane
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: 3-cis-aminocyclohexane
<220> FEATURE:
<221> NAME/KEY: MOD_RES
<222> LOCATION: (10)..(10)
<223> OTHER INFORMATION: 6-aminohexanoic acid

<400> SEQUENCE: 41

Arg Arg Xaa Xaa Xaa Xaa Xaa Xaa Arg Xaa
1               5                   10

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane
<220> FEATURE:
<221> NAME/KEY: MOD_RES
<222> LOCATION: (3)..(3)
<223> OTHER INFORMATION: 3-cis-aminocyclohexane
<220> FEATURE:
<221> NAME/KEY: MOD_RES
<222> LOCATION: (4)..(4)
<223> OTHER INFORMATION: 3-cis-aminocyclohexane
<220> FEATURE:
<221> NAME/KEY: MOD_RES
<222> LOCATION: (5)..(5)
<223> OTHER INFORMATION: 3-cis-aminocyclohexane
<220> FEATURE:
<221> NAME/KEY: MOD_RES
<222> LOCATION: (6)..(6)
<223> OTHER INFORMATION: cis-2-aminocyclopentane-1-carbonyl
<220> FEATURE:
<221> NAME/KEY: MOD_RES
<222> LOCATION: (7)..(7)
<223> OTHER INFORMATION: 3-cis-aminocyclohexane
<220> FEATURE:
<221> NAME/KEY: MOD_RES
<222> LOCATION: (8)..(8)
<223> OTHER INFORMATION: cis-2-aminocyclopentane-1-carbonyl
<220> FEATURE:
<221> NAME/KEY: MOD_RES
<222> LOCATION: (10)..(10)
<223> OTHER INFORMATION: 6-aminohexanoic acid

<400> SEQUENCE: 42

Arg Xaa Xaa Xaa Xaa Xaa Xaa Xaa Arg Xaa
1               5                   10
```

```
<210> SEQ ID NO 43
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: MOD_RES
<222> LOCATION: (14)..(14)
<223> OTHER INFORMATION: Beta-Ala

<400> SEQUENCE: 43

Arg Xaa Arg Arg Xaa Arg Arg Xaa Arg Arg Xaa Arg Xaa Ala
1               5                   10

<210> SEQ ID NO 44
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(4)
<223> OTHER INFORMATION: D-Arg
```

```
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: MOD_RES
<222> LOCATION: (14)..(14)
<223> OTHER INFORMATION: Beta-Ala

<400> SEQUENCE: 44

Arg Xaa Arg Arg Ala Arg Arg Xaa Arg Arg Ala Arg Xaa Ala
1               5                   10

<210> SEQ ID NO 45
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Phe Ser
1

<210> SEQ ID NO 46
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Phe Ser Gln
1

<210> SEQ ID NO 47
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47
```

Phe Ser Gln Lys
1

<210> SEQ ID NO 48
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Asp" or "Lys" or "Ser" or "Thr"
<220> FEATURE:
<221> NAME/KEY: MOD_RES
<222> LOCATION: (4)..(4)
<223> OTHER INFORMATION: Beta-Ala
<220> FEATURE:
<221> NAME/KEY: VARIANT
<222> LOCATION: (4)..(4)
<223> OTHER INFORMATION: /replace="Beta-Gly"
<220> FEATURE:
<221> NAME/KEY: misc_feature
<222> LOCATION: (1)..(4)
<223> OTHER INFORMATION: /note="Variant residues given in the sequence
      have no preference with respect to those in the annotations
      for variant positions"

<400> SEQUENCE: 48

Phe Xaa Glu Ala
1

<210> SEQ ID NO 49
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Phe Lys Glu
1

<210> SEQ ID NO 50
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Phe Ala Glu
1

<210> SEQ ID NO 51
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:

```
                          Synthetic peptide"

<400> SEQUENCE: 51

Phe Val Glu
1

<210> SEQ ID NO 52
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Phe Leu Glu
1

<210> SEQ ID NO 53
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Phe Ser Glu
1

<210> SEQ ID NO 54
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Citruline

<400> SEQUENCE: 54

Val Xaa Glu
1

<210> SEQ ID NO 55
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
```

```
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 55

Arg Xaa Arg Arg Ala Arg Arg Xaa Arg Arg Ala Arg Xaa Phe Lys Glu
1               5                   10                  15

Gly

<210> SEQ ID NO 56
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
```

```
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: MOD_RES
<222> LOCATION: (16)..(16)
<223> OTHER INFORMATION: D-Glu

<400> SEQUENCE: 56

Arg Xaa Arg Arg Ala Arg Arg Xaa Arg Arg Ala Arg Xaa Phe Asp Glu
1               5                   10                  15

Glu Gly

<210> SEQ ID NO 57
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
```

```
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid

<400> SEQUENCE: 57

Glu Arg Xaa Arg Arg Ala Arg Arg Xaa Arg Arg Ala Arg Xaa Phe Lys
1               5                   10                  15

Gly

<210> SEQ ID NO 58
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
```

```
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid

<400> SEQUENCE: 58

Glu Arg Xaa Arg Arg Ala Arg Arg Xaa Arg Arg Ala Arg Xaa Phe Lys
1               5                   10                  15

Gly

<210> SEQ ID NO 59
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
```

<222> LOCATION: (14)..(14)
<223> OTHER INFORMATION: 6-aminohexanoic acid

<400> SEQUENCE: 59

Glu Arg Xaa Arg Arg Ala Arg Arg Xaa Arg Arg Ala Arg Xaa Phe Lys
1               5                   10                  15

Glu Gly

<210> SEQ ID NO 60
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid
<220> FEATURE:
<221> NAME/KEY: MOD_RES
<222> LOCATION: (17)..(17)
<223> OTHER INFORMATION: D-Glu

<400> SEQUENCE: 60

Glu Arg Xaa Arg Arg Ala Arg Arg Xaa Arg Arg Ala Arg Xaa Phe Lys

Glu Glu Gly

<210> SEQ ID NO 61
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid

<400> SEQUENCE: 61

Glu Glu Arg Xaa Arg Arg Ala Arg Arg Xaa Arg Arg Ala Arg Xaa Phe
1               5                   10                  15

Lys Gly

<210> SEQ ID NO 62

```
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid

<400> SEQUENCE: 62

Glu Glu Arg Xaa Arg Arg Ala Arg Arg Xaa Arg Arg Ala Arg Xaa Phe
1               5                   10                  15

Lys Gly

<210> SEQ ID NO 63
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid

<400> SEQUENCE: 63

Glu Glu Arg Xaa Arg Arg Ala Arg Arg Xaa Arg Arg Ala Arg Xaa Phe
1               5                   10                  15

Lys Glu Gly

<210> SEQ ID NO 64
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Glu
<220> FEATURE:
```

```
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid
<220> FEATURE:
<221> NAME/KEY: MOD_RES
<222> LOCATION: (18)..(18)
<223> OTHER INFORMATION: D-Glu

<400> SEQUENCE: 64

Glu Glu Arg Xaa Arg Arg Ala Arg Arg Xaa Arg Arg Ala Arg Xaa Phe
1               5                   10                  15

Lys Glu Glu Gly
            20

<210> SEQ ID NO 65
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
```

```
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 65

Arg Xaa Arg Arg Ala Arg Arg Xaa Arg Arg Ala Arg Xaa Phe Lys Gly
1               5                   10                  15

<210> SEQ ID NO 66
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
```

```
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 66

Arg Xaa Arg Arg Ala Arg Arg Xaa Arg Arg Ala Arg Xaa Phe Lys Gly
1               5                   10                  15

<210> SEQ ID NO 67
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
```

```
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 67

Arg Xaa Arg Arg Ala Arg Arg Xaa Arg Arg Ala Arg Xaa Phe Lys Gly
 1               5                  10                  15

<210> SEQ ID NO 68
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
```

```
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 68

Arg Xaa Arg Arg Ala Arg Arg Xaa Arg Arg Ala Arg Xaa Phe Lys Gly
1               5                   10                  15

<210> SEQ ID NO 69
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: misc_feature
```

-continued

<222> LOCATION: (16)..(17)
<223> OTHER INFORMATION: /note="Residues at these positions are
      non-consecutive and are separated by a PMO molecule"

<400> SEQUENCE: 69

Arg Xaa Arg Arg Ala Arg Arg Xaa Arg Arg Ala Arg Xaa Phe Lys Glu
1               5                   10                  15

Gly

<210> SEQ ID NO 70
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: MOD_RES
<222> LOCATION: (16)..(16)
<223> OTHER INFORMATION: D-Glu
<220> FEATURE:
<221> NAME/KEY: misc_feature
<222> LOCATION: (16)..(18)

<223> OTHER INFORMATION: /note="Residues at these positions are
     non-consecutive and are separated by a PMO molecule"

<400> SEQUENCE: 70

Arg Xaa Arg Arg Ala Arg Arg Xaa Arg Arg Ala Arg Xaa Phe Asp Glu
1               5                   10                  15

Glu Gly

<210> SEQ ID NO 71
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"
<220> FEATURE:
<221> NAME/KEY: misc_feature
<222> LOCATION: (1)..(2)
<223> OTHER INFORMATION: /note="Residues at these positions are
     non-consecutive and are separated by a PMO molecule"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid

<400> SEQUENCE: 71

Glu Arg Xaa Arg Arg Ala Arg Arg Xaa Arg Arg Ala Arg Xaa Phe Lys
1               5                   10                  15

Gly

<210> SEQ ID NO 72
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(2)
<223> OTHER INFORMATION: /note="Residues at these positions are
      non-consecutive and are separated by a PMO molecule"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid

<400> SEQUENCE: 72

Glu Arg Xaa Arg Arg Ala Arg Arg Xaa Arg Arg Ala Arg Xaa Phe Lys
1               5                   10                  15

Gly

```
<210> SEQ ID NO 73
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(2)
<223> OTHER INFORMATION: /note="Residues at these positions are
      non-consecutive and are separated by a PMO molecule"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid
<220> FEATURE:
<221> NAME/KEY: misc_feature
<222> LOCATION: (17)..(18)
<223> OTHER INFORMATION: /note="Residues at these positions are
      non-consecutive and are separated by a PMO molecule"

<400> SEQUENCE: 73

Glu Arg Xaa Arg Arg Ala Arg Xaa Arg Arg Ala Arg Xaa Phe Lys
1               5                   10                  15

Glu Gly
```

```
<210> SEQ ID NO 74
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(2)
<223> OTHER INFORMATION: /note="Residues at these positions are
      non-consecutive and are separated by a PMO molecule"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid
<220> FEATURE:
<221> NAME/KEY: MOD_RES
<222> LOCATION: (17)..(17)
<223> OTHER INFORMATION: D-Glu
<220> FEATURE:
<221> NAME/KEY: misc_feature
<222> LOCATION: (17)..(19)
<223> OTHER INFORMATION: /note="Residues at these positions are
      non-consecutive and are separated by a PMO molecule"

<400> SEQUENCE: 74

Glu Arg Xaa Arg Arg Ala Arg Arg Xaa Arg Arg Ala Arg Xaa Phe Lys
```

Glu Glu Gly

<210> SEQ ID NO 75
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: misc_feature
<222> LOCATION: (1)..(3)
<223> OTHER INFORMATION: /note="Residues at these positions are non-consecutive and are separated by a PMO molecule"
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid

<400> SEQUENCE: 75

Glu Glu Arg Xaa Arg Arg Ala Arg Arg Xaa Arg Arg Ala Arg Xaa Phe
1               5                   10                  15

Lys Gly

<210> SEQ ID NO 76
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: misc_feature
<222> LOCATION: (1)..(3)
<223> OTHER INFORMATION: /note="Residues at these positions are non-consecutive and are separated by a PMO molecule"
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid

<400> SEQUENCE: 76

Glu Glu Arg Xaa Arg Arg Ala Arg Arg Xaa Arg Arg Ala Arg Xaa Phe
1               5                   10                  15

Lys Gly

```
<210> SEQ ID NO 77
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: misc_feature
<222> LOCATION: (1)..(3)
<223> OTHER INFORMATION: /note="Residues at these positions are
      non-consecutive and are separated by a PMO molecule"
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid
<220> FEATURE:
<221> NAME/KEY: misc_feature
<222> LOCATION: (18)..(19)
<223> OTHER INFORMATION: /note="Residues at these positions are
      non-consecutive and are separated by a PMO molecule"

<400> SEQUENCE: 77
```

-continued

Glu Glu Arg Xaa Arg Arg Ala Arg Arg Xaa Arg Arg Ala Arg Xaa Phe
1               5                   10                  15

Lys Glu Gly

<210> SEQ ID NO 78
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Glu
<220> FEATURE:
<221> NAME/KEY: misc_feature
<222> LOCATION: (1)..(3)
<223> OTHER INFORMATION: /note="Residues at these positions are
      non-consecutive and are separated by a PMO molecule"
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: 6-aminohexanoic acid
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: Beta-Ala
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: 6-aminohexanoic acid
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: D-Arg
<220> FEATURE:
<221> NAME/KEY: MOD_RES
<222> LOCATION: (15)..(15)
<223> OTHER INFORMATION: 6-aminohexanoic acid
<220> FEATURE:
<221> NAME/KEY: MOD_RES
<222> LOCATION: (18)..(18)

```
<223> OTHER INFORMATION: D-Glu
<220> FEATURE:
<221> NAME/KEY: misc_feature
<222> LOCATION: (18)..(20)
<223> OTHER INFORMATION: /note="Residues at these positions are
      non-consecutive and are separated by a PMO molecule"

<400> SEQUENCE: 78

Glu Glu Arg Xaa Arg Arg Ala Arg Arg Xaa Arg Arg Ala Arg Xaa Phe
1               5                   10                  15

Lys Glu Glu Gly
            20

<210> SEQ ID NO 79
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 79
```

```
Arg Xaa Arg Arg Ala Arg Arg Xaa Arg Arg Ala Arg Xaa Phe Lys Gly
1               5                   10                  15
```

<210> SEQ ID NO 80
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 80

```
Arg Xaa Arg Arg Ala Arg Arg Xaa Arg Arg Ala Arg Xaa Phe Lys Gly
1               5                   10                  15
```

<210> SEQ ID NO 81
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: misc_feature
<222> LOCATION: (16)..(17)
<223> OTHER INFORMATION: /note="Residues at these positions are
      non-consecutive and are separated by a (PEG)2-PMO molecule"

<400> SEQUENCE: 81

Arg Xaa Arg Arg Xaa Arg Arg Xaa Arg Xaa Arg Xaa Phe Lys Glu
1               5                   10                  15

Gly

<210> SEQ ID NO 82
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
```

```
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: MOD_RES
<222> LOCATION: (14)..(14)
<223> OTHER INFORMATION: Beta-Ala

<400> SEQUENCE: 82

Arg Xaa Arg Arg Ala Arg Arg Xaa Arg Arg Ala Arg Xaa Ala Ala
1               5                   10                  15

<210> SEQ ID NO 83
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 83
cagaattctg ccaattgctg ag                                          22

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 84
ttcttcagct tgtgtcatcc                                        20

<210> SEQ ID NO 85
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
ggccaaacct cggcttacct gaaat                                  25

<210> SEQ ID NO 86
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES -continued

```
<222> LOCATION: (13)..(13)
<223> OTHER INFORMATION: 6-aminohexanoic acid

<400> SEQUENCE: 86

Arg Xaa Arg Arg Xaa Arg Xaa Arg Arg Xaa Arg Xaa Glu Gly
1               5                   10                  15

<210> SEQ ID NO 87
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: misc_feature
<222> LOCATION: (14)..(15)
<223> OTHER INFORMATION: /note="Residues at these positions are
      non-consecutive and are separated by a (PEG)2-PMO molecule"

<400> SEQUENCE: 87

Arg Xaa Arg Arg Xaa Arg Xaa Arg Arg Xaa Arg Xaa Glu Gly
1               5                   10                  15
```

```
<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 88

Arg Xaa Arg Arg Xaa Arg Arg Xaa Arg Xaa Arg Xaa Ala
1               5                   10

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
```

```
<222> LOCATION: (1)..(2)
<223> OTHER INFORMATION: /note="Residues at these positions are
      non-consecutive and are separated by a PMO molecule"
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (3)..(3)
<223> OTHER INFORMATION: 6-aminohexanoic acid
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Arg
<220> FEATURE:
<221> NAME/KEY: MOD_RES
<222> LOCATION: (6)..(6)
<223> OTHER INFORMATION: Beta-Ala
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: D-Arg
<220> FEATURE:
<221> NAME/KEY: MOD_RES
<222> LOCATION: (9)..(9)
<223> OTHER INFORMATION: 6-aminohexanoic acid
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: D-Arg
<220> FEATURE:
<221> NAME/KEY: MOD_RES
<222> LOCATION: (12)..(12)
<223> OTHER INFORMATION: Beta-Ala
<220> FEATURE:
<221> NAME/KEY: MOD_RES
<222> LOCATION: (13)..(13)
<223> OTHER INFORMATION: D-Arg
<220> FEATURE:
<221> NAME/KEY: MOD_RES
<222> LOCATION: (14)..(14)
<223> OTHER INFORMATION: 6-aminohexanoic acid

<400> SEQUENCE: 89

Glu Arg Xaa Arg Arg Ala Arg Arg Xaa Arg Arg Ala Arg Xaa Phe Lys
1               5                   10                  15

Gly

<210> SEQ ID NO 90
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
```

```
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid
<220> FEATURE:
<221> NAME/KEY: misc_feature
<222> LOCATION: (14)..(15)
<223> OTHER INFORMATION: /note="Residues at these positions are
      non-consecutive and are separated by a PMO molecule"

<400> SEQUENCE: 90

Arg Xaa Arg Arg Ala Arg Arg Xaa Arg Arg Ala Arg Xaa Glu Gly
1               5                   10                  15

<210> SEQ ID NO 91
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
```

```
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: Beta-Ala
<220> FEATURE:
<221> NAME/KEY: MOD_RES
<222> LOCATION: (12)..(12)
<223> OTHER INFORMATION: D-Arg

<400> SEQUENCE: 91

Arg Xaa Arg Arg Ala Arg Arg Xaa Arg Arg Ala Arg Phe Lys Glu Gly
1               5                   10                  15

<210> SEQ ID NO 92
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
```

```
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 92

Arg Xaa Arg Arg Xaa Arg Arg Xaa Arg Arg Xaa Arg Xaa Ala
1               5                   10

<210> SEQ ID NO 93
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
```

-continued

```
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg
<220> FEATURE:
<221> NAME/KEY: MOD_RES
<222> LOCATION: (13)..(13)
<223> OTHER INFORMATION: 6-aminohexanoic acid

<400> SEQUENCE: 93

Arg Xaa Arg Arg Xaa Arg Arg Xaa Arg Arg Xaa Arg Xaa Glu Gly
1               5                   10                  15

<210> SEQ ID NO 94
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: 6-aminohexanoic acid
<220> FEATURE:
<221> NAME/KEY: MOD_RES
<222> LOCATION: (3)..(3)
<223> OTHER INFORMATION: D-Arg
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: 6-aminohexanoic acid
<220> FEATURE:
<221> NAME/KEY: MOD_RES
<222> LOCATION: (6)..(6)
<223> OTHER INFORMATION: D-Arg
<220> FEATURE:
<221> NAME/KEY: MOD_RES
<222> LOCATION: (7)..(7)
<223> OTHER INFORMATION: D-Arg
<220> FEATURE:
<221> NAME/KEY: MOD_RES
<222> LOCATION: (8)..(8)
<223> OTHER INFORMATION: 6-aminohexanoic acid
<220> FEATURE:
<221> NAME/KEY: MOD_RES
<222> LOCATION: (9)..(9)
<223> OTHER INFORMATION: D-Arg
<220> FEATURE:
<221> NAME/KEY: MOD_RES
<222> LOCATION: (10)..(10)
<223> OTHER INFORMATION: D-Arg
<220> FEATURE:
<221> NAME/KEY: MOD_RES
<222> LOCATION: (11)..(11)
<223> OTHER INFORMATION: 6-aminohexanoic acid
<220> FEATURE:
<221> NAME/KEY: MOD_RES
<222> LOCATION: (12)..(12)
<223> OTHER INFORMATION: D-Arg

<400> SEQUENCE: 94

Arg Xaa Arg Arg Xaa Arg Arg Xaa Arg Arg Xaa Arg Phe Lys Glu Gly
1               5                   10                  15
```

```
<210> SEQ ID NO 95
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Phe Ser Gln Gly
1

<210> SEQ ID NO 96
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Asp" or "Lys" or "Ser" or "Thr"
<220> FEATURE:
<221> NAME/KEY: MOD_RES
<222> LOCATION: (4)..(4)
<223> OTHER INFORMATION: Beta-Ala
<220> FEATURE:
<221> NAME/KEY: misc_feature
<222> LOCATION: (1)..(4)
<223> OTHER INFORMATION: /note="Variant residues given in the sequence
      have no preference with respect to those in the annotations
      for variant positions"

<400> SEQUENCE: 96

Phe Xaa Glu Ala
1
```

MULTIPLE OLIGONUCLEOTIDE MOIETIES ON PEPTIDE CARRIER

CROSS-REFERENCE TO RELATED APPLICATION

This application is a continuation of U.S. patent application Ser. No. 15/313,405, which adopts the international filing date of May 22, 2015, which is a National Phase application under 35 U.S.C. § 371 of International Application No. PCT/US2015/032142, filed May 22, 2015, which claims the benefit of priority U.S. Provisional Patent Application No. 62/002,296, filed May 23, 2014, which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952031101seqlist.txt, date recorded: Feb. 1, 2019, size: 80 KB).

DESCRIPTION OF THE INVENTION

Field of the Invention

The present disclosure relates to antisense oligonucleotides (AONs), such as, but not limited to, phosphorodiamidate morpholino oligonucleotides (PMOs). The present disclosure further relates to the conjugation of multiple PMOs to cationic cell penetrating peptides (CPPs) to enhance the uptake of PMOs into tissues of interest, such as skeletal and cardiac muscle cells. The present disclosure encompasses such conjugates, as well as methods of their use, including for example, using them to modulate gene expression. The present disclosure further includes methods of treating various disease states by administering to a human or animal in need thereof said multiple PMO-CPP conjugates.

SUMMARY OF THE INVENTION

AONs have been shown to successfully modulate gene expression both in vitro and in vivo in various disease states, including for example Duchenne muscular dystrophy (DMD). In particular, PMOs designed to target and remove the in-frame exon 23 have been successful at restoring dystrophin function in the mdx mouse model of DMD.

However, AONs have also been shown to exhibit a poor uptake profile in skeletal and cardiac muscle cells, which hampers their ability to affect mRNA transcription and translation. (WO 2009/147368) In particular, PMOs, 2-O-methyl oligonucleotides, and peptide nucleic acids (PNAs) do not appreciably accumulate in skeletal muscle and their uptake in heart muscle is negligible.

Cell penetrating peptides (CPPs) were discovered in the late 1980s. [Frankel and Pabo Cell 1988; Green and Loewenstein Cell 1988] These compounds help transport different moieties across cell membranes that would otherwise have difficulty crossing the cell membrane on their own. About 20 years after the discovery of CPPs, several research studies showed that CPPs named "K" (RXRRXRRXRRXRXB, SEQ ID NO.: 43) and "B" (RXRRBRRXRRBRXB, SEQ ID NO.: 44) tethered to a single PMO designed to skip exon 23 (PMO23) of the mRNA encoding for dystrophin greatly increased exon skipping in skeletal and heart muscle using the mdx mouse model. [Jearawiriyapaisarn et al Mol Therapy 2008] The results of these studies demonstrated that a single PMO-CPP conjugate exhibited >85% skipping of exon 23 in skeletal muscle, whereas the naked PMO compound resulted <15% exon skipping. A modest effect was also observed in cardiac muscle (~60%) in comparison to the naked PMO, which does not effect exon 23 skipping in cardiac muscle. [Op. Cit.]

WO 2009/144481 relates to a construct comprising a cell delivery peptide in a complex with a biologically active compound, such as an AON, including for example a PMO. WO 2004/097017 (US 2004/0265879 and US 2009/0082547) relates to method for enhancing delivery of molecules, including disclosing a conjugate of a biological agent, such as a PMO, and a peptide transporter. WO 2009/147368 discloses novel CPPs, which may be conjugated to for example PNAs and PMOs. US 2010/0130591 discloses PMOs capable of binding to a selected target site in the human dystrophin gene that may be conjugated to a CPP.

Despite the enhanced efficacy observed with single PMO-CPP conjugates, the conjugates possess an increased toxicity compared to the naked PMOs. [cite] For example, the maximum tolerated dose for the mdx mouse exon 23 skipping studies using CPP-PMO23B or CPP-PMO23K was shown to be 30 mg/kg. At amounts of 60 mg/kg, the mice lost weight and doses of 150 mg/kg were lethal. [Amantana et al Bioconjugate Chem 2007] In contrast, the naked PMO23 could be administered in amounts as high as 250 mg/kg without any noticeable toxic effects [Op. Cit.]. WO 2009/005793 discloses that CPPs having below four X (6-aminohexanoic acid) residues, including CPP "B" exhibited lower toxicity than previously identified CPPs. As shown above, however, these CPPs coupled to a single PMO still exhibit unacceptable toxicity compared to the naked PMOs [Op Cit. and Moulton and Moulton Biochemica et Biophysica Acta 2010].

It is accordingly a primary object of the present disclosure to overcome the problems of poor uptake of naked PMOs and the increased toxicity associated with single PMO-CPP constructs. Multiple conjugation sites on the CPP are introduced by adding glutamic acid in the D- or L-enantiomeric position to reduce stearic hindrance of multiple PMOs in close proximity at the termini of the CPP. The use of a peptidase cleavage site with the amino acids Phenylalanine-Lysine at the P1, −P1 positions is introduced between the CPP and the PMO. Cleavage of the peptidase cleavage site releases the PMO from the CPP. For example, the CPP may be attached to the PMO via a maleimide esterized linker with an enzyme cleavage site Phenylalanine-Lysine or Valine-Citruline that could be introduced at a cysteine position. The CPP may also be attached via an amide bond.

Internalization into the cell using the peptide may result in an intracellular protease, including a lysosomal enzyme, cleaving the cleavage site and the free PMO would have lower stearic hindrance from the peptide bound conjugate. This lower stearic constraint could increase exon skipping efficiency with less toxicity to the nucleus and cytosol.

In at least one aspect this is achieved by the discovery of multiple PMO-CPP conjugates as further described herein. The present disclosure also contemplates a method for increasing the safety margin of a single PMO-CPP conjugate by substituting conjugates according to the present disclosure. The present disclosure further includes methods of modulating gene expression, such as those encoding for glycogen synthase (GYS1 or GYS2), transforming growth factor (TGFβ), matrix metallopeptidase (MM P2 or MMP9), osteopontin, myotonic dystrophy protein kinase (DMPK), Elav-Like Family Member 2 (also known as CUG Triplet Repeat RNA-Binding Protein or CUGBP), double homeobox 4 (DUX4), and/or (Frzl). The following genes: glycogen synthase (GYS1 or GYS2), transforming growth factor (TGFβ), matrix metallopeptidase (MMP2 or MMP9), osteopontin, myotonic dystrophy protein kinase (DMPK), Elav-Like Family Member 2 (also known as CUG Triplet Repeat RNA-Binding Protein or CUGBP), double homeobox 4 (DUX4), and/or (Frzl) may be targeted via the PMO-CPP conjugates of the present invention to mediate exon skipping to create a frame shift mutation. Any frame shift mutation could result in the functional reduction in the amount of mRNA targeted by the AON sequence. The present disclosure also includes within its scope the use of multiple PMO-CPP conjugates for the suppression of microRNAs in various disease states. In another aspect, the present disclosure includes methods of treating various diseases and/or conditions, such as those associated with the genes and microRNAs mentioned above.

Additional objects and advantages of the present disclosure will be set forth in part in the description which follows, and in part will naturally flow from the description, or may be learned by practice of the disclosed embodiments. The objects and advantages of the present disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIG. 1 is a schematic of the configurations of the multiple AONs attached to a single CPP.

DESCRIPTION OF THE EMBODIMENTS/DETAILED DESCRIPTION OF THE INVENTION

Figure 2:
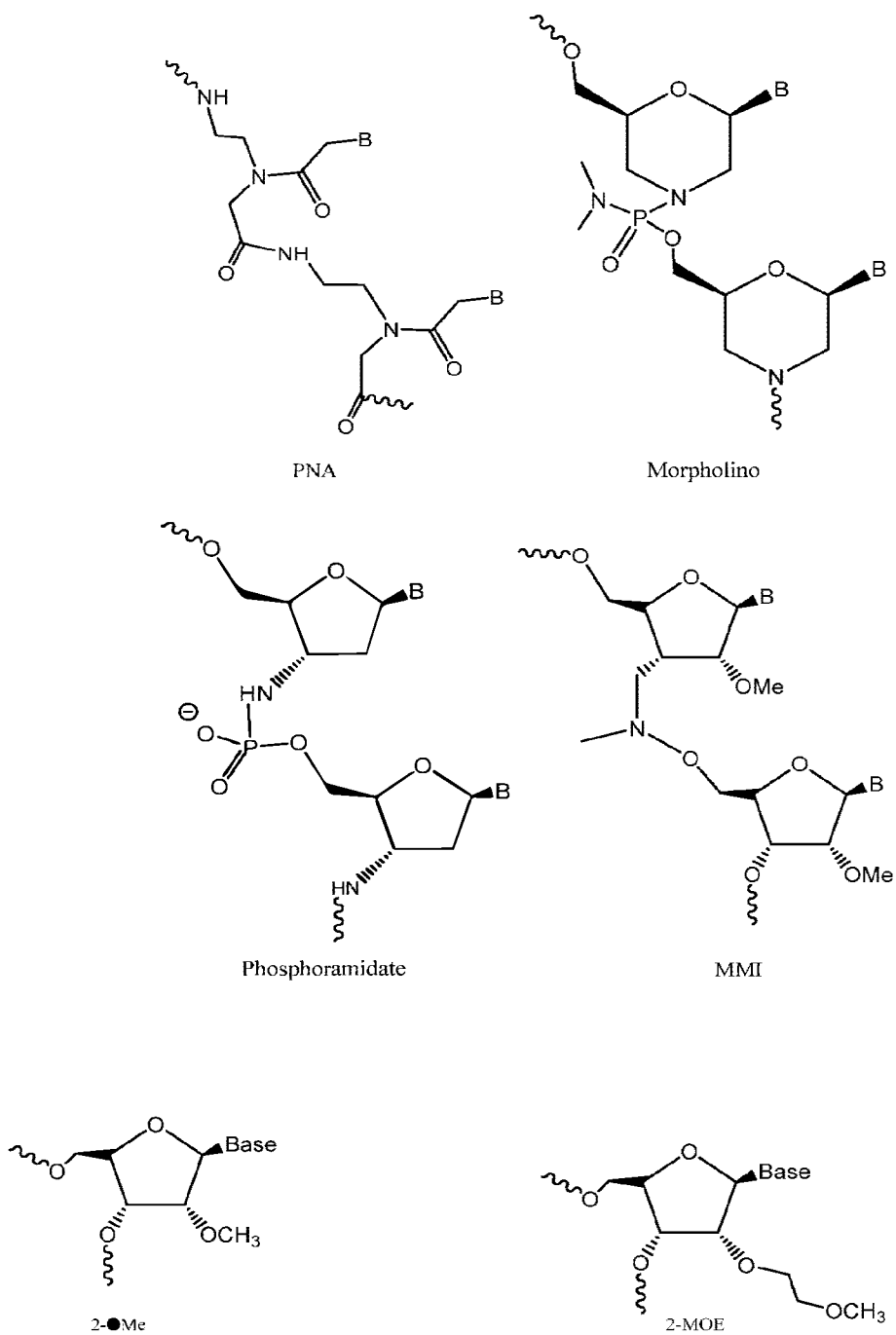
FIG. 2 is a schematic of the various antisense oligonucleotide subunits that could be oligomerized and used in a multiple AON configuration of the instant invention.

As mentioned above, it is one object of the present disclosure to improve the safety profile of single PMO-CPP conjugates without compromising the conjugate's uptake into a target cell. It is generally preferable to have at least a 10-fold safety margin between the efficacious dose and the no adverse effect level (NOAEL). In the mdx/exon 23 experiments described above, the efficacious dose was found to be 30 mg/kg and the NOAEL was also 30 mg/kg. As a result, there was little or no safety margin. In at least one embodiment of the present disclosure, the multiple PMO-CPP conjugate has a safety margin that is better than the mdx/exon 23 experiments described above, such as better than 2-fold, such as better than 5-fold, such as better than 6-fold, such as better than 10-fold. A 10-fold safety margin means that the efficacious dose is 10 times lower than the NOAEL. Thus, when tested in the appropriate model, the multiple PMO-CPP conjugates according to the present disclosure may have a safety margin of at least 2-fold better than the corresponding single PMO-CPP conjugate. The present invention comprises multiple AON, including PMO AON, attached to a single CPP.

In at least one embodiment of the present disclosure the multiple AON-CPP conjugate further comprises a cleavable linker. In some embodiments, the linker is a sequence that contains a cleavage motif. In some embodiments, the cleavage motif can be cleaved by any hydrolytic enzyme. In some embodiments, the cleavage motif can be cleaved by a peptidase or protease such as cathepsin or trypsin. In some embodiments, the linker can be designed to include a cleavage motif recognized by a particular serine protease, threonine protease, cysteine protease, aspartate protease, glutamic acid protease, or metalloprotease, or a group of more than one peptidase. In some embodiments, the linker may include two or more cleavage motifs that are overlapping or nonoverlapping. In some embodiments, the linker may contain no cleavage motifs. In some embodiments, the linker may be designed so that less than 100%, less than 75%, less than 50%, or less than 10% of the linkers are cleaved. In some embodiments, the linker is designed so that greater than 90% or 99% of the linkers are cleaved.

In at least one embodiment of the present disclosure the multiple AON-CPP conjugate further comprises a cleavable linker, such as FK at the P1/P1' position or in another embodiment, FX at the P1/P1' position where X is any naturally occurring amino acid. The cleavable linker, wherein said linker is cleavable by a hydrolytic enzyme such as for example cathepsin, can occur in between the AON and the CPP or it can occur in a sequence such as AON-cleavable linker-AON-cleavable linker-CPP. In another embodiment, the multiple PMO-CPP conjugate further comprises a cleavable linker, such as cathepsin, or FK at the P1/P1' position or in another embodiment, FX at the P1/P1' position where X is any naturally occurring amino acid. The cleavable linker can occur in between the PMO and the CPP or it can occur in a sequence such as PMO-cleavable linker-PMO-cleavable linker-CPP, e.g. as PMO-cathepsin linker-PMO-cathepsin linker-CPP. The present disclosure does not limit the order of the AONs (including PMOs), cleavable linkers, and CPP, and one skilled in the art will be able to design a suitable multiple AON-CPP conjugate having at least one cathepsin cleavage site according to the claims using the information disclosed herein.

It was surprisingly found that multiple PMO-CPP conjugates with cleavable linker sites according to the present disclosure in some instances exhibited even better efficacy than multiple PMO-CPP conjugates without them. This result was unexpected because it has been shown that single PMO-CPP conjugates are taken up into the lysosome and can remain trapped there if the peptide moiety is degraded too rapidly. In other words, if the CPP part of the single PMO-CPP conjugate is degraded quickly, the PMO becomes trapped in the lysosome and cannot reach its cellular target, thus decreasing efficacy. (Youngblood et al. 2007) As a result of this phenomenon, it would have been expected that adding a cleavable linker site in the conjugate would facilitate the CPP's degradation, leading to a decrease in efficacy. This was not the case; however, in certain multiple PMO-CPP conjugates with cleavable linker sites according to the present invention as will be described in the specific examples below. Thus, in at least one embodiment of the present disclosure a multiple PMO-CPP conjugate has at least one cleavable linker site. In at least another embodiment of the present disclosure a multiple PMO-CPP conjugate has at least one cathepsin cleavable linker site.

The present disclosure further includes methods of modulating gene expression, such as those encoding for glycogen synthase (GYS1 or GYS2), transforming growth factor (TGFβ), matrix metallopeptidase (MMP2 or MMP9), osteopontin, myotonic dystrophy protein kinase (DMPK), Elav-Like Family Member 2 (also known as CUG Triplet Repeat RNA-Binding Protein or CUGBP), double homeobox 4 (DUX4), and/or (Frzl), wherein the multiple AON-CPP conjugates of the present invention to mediate exon skipping to create a frame shift mutation. Any frame shift mutation could result in the knock-down of mRNA targeted. The present disclosure also includes within its scope the use of multiple PMO-CPP conjugates for the suppression of microRNAs in various disease states. In at least one embodiment, the present disclosure includes methods of treating various diseases and/or conditions, such as those associated with the genes and microRNAs mentioned above. The multiple CPP-PMO conjugates of the present disclosure may be administered to a human or animal in need thereof by any suitable means. Administration to a human or animal subject may be selected from parenteral, intramuscular, intracerebral, intravascular, subcutaneous, or transdermal. In at least one embodiment, the route of administration is by injection, such as intravenously or intramuscularly. A treating physician will be able to determine the appropriate route of administration.

When employed as pharmaceuticals, the multiple CPP-PMO conjugates antisense oligonucleotides disclosed herein can be formulated with a pharmaceutically acceptable excipient or carriers to be formulated into a pharmaceutical composition.

When employed as pharmaceuticals, the multiple CPP-PMO conjugates antisense oligonucleotides can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the multiple CPP-PMO conjugates antisense oligonucleotides associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 mg to about 100 mg or more, such as any of about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, or about 5 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The multiple CPP-PMO conjugates antisense oligonucleotides are effective over a wide dosage range and are generally administered in a therapeutically effective amount. It will be understood, however, that the amount of the multiple CPP-PMO conjugates antisense oligonucleotides actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient/multiple CPP-PMO conjugates antisense oligonucleotide is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may also be administered, orally or nasally, from devices which deliver the formulation in an appropriate manner.

The multiple CPP-AON, including CPP-PMO, conjugates according to the present disclosure may be administered in a daily dose ranging from 1-200_mg/kg, such as from 10_-50 mg/kg. The CPP-AON conjugate, including CPP-PMO, may be administered in bolus form or over a prolonged injection period. For example, the daily dosage can be administered in one bolus dose. Alternatively, the daily dosage can be administered via injection, such as intravenously, or subcutaneously. In another embodiment the daily dosage can be divided into several administrations, such as two times, three times, or four times a day. Dosing may be repeated daily as needed as determined by the treating physician. Treatment may be short-term, such as for less than 6 months. In another embodiment, treatment may be long-term, such as greater than 6 months, such as greater than 1 year, such as greater than 10 years, such as over the lifetime of the human or animal in need of treatment.

The multiple AON conjugate, including PMO-CPP, conjugates of the present disclosure specifically hybridize with one or more of pre-mRNA, mRNA, and/or microRNA or long non-coding RNA transcribed from a target gene or locus. As used herein, a multiple PMO-CPP conjugate specifically hybridizes to a target polynucleotide, such as pre-mRNA or mRNA, when the multiple PMO-CPP conjugate hybridizes to the target under physiological conditions. In the context of the present disclosure, hybridization occurs via hydrogen bonding, which may be Watson-Crick, Hoogsteen or reversed Hoogsteen hydrogen bonding, between complementary purine and pyrimidine bases. For example, adenine (A) and thymine (T) are complementary nucleobases which pair through the formation of hydrogen bonds. According to the present disclosure the PMO portion of the multiple PMO-CPP conjugate specifically hybridizes to the target nucleotide. The CPP moiety can remain tethered to the multiple PMO-CPP conjugate or it can be cleaved prior to hybridization, such as for example at a cathepsin cleavage site.

PMO compounds of the present disclosure are complementary to a target polynucleotide, such as pre-mRNA, mRNA, or microRNA, or long non-coding RNA when hybridization occurs according to generally accepted base-pairing rules, e.g., adenine (A)-thymine (T), cytosine (C)-guanine (G), adenine (A)-uracil (U). In particular, "complementary" as used herein refers to the capacity for precise pairing between two nucleobases. For example, if a base (B) at a certain position of a PMO compound is capable of hydrogen binding with a nucleotide at the same position of a pre-mRNA or mRNA molecule, then the PMO and the target polynucleotide molecule are considered to be complementary to each other at that position. The PMO compound and target polynucleotide molecule are complementary to each other when a sufficient number of corresponding positions in each molecule are occupied by bases that can hydrogen bond with each other. Thus, "specifically hybridizable" and "complementary" are terms which are used to indicate a sufficient degree of complementarity or precise pairing such that stable and specific binding occurs between the PMO and the polynucleotide target. Absolute complementarity, i.e., a 100% complementary base pair match, is not necessary as long as the heteroduplex formed between the target polynucleotide molecule and the PMO has the desired stability sufficient to provoke the desired effect. According to the present disclosure, a PMO is specifically hybridizable when binding of the PMO compound to the target polynucleotide molecule changes the normal function of the target polynucleotide molecule, and there is a sufficient degree of complementarity to avoid undesirable non-specific binding of the PMO to a non-target sequence under conditions in which specific binding is desired, for example under physiological conditions for in vivo applications or under conditions in which assays are performed for in vitro applications.

Such hybridization between a PMO and a target polynucleotide molecule, such as mRNA or pre-mRNA, interferes with their normal functions, such as translation of protein from the mRNA and splicing of the pre-mRNA to yield one or more mRNA species. In at least one embodiment of the present disclosure, the hybridization between the PMO and pre-mRNA affects the splicing of the pre-mRNA to form RNA. In another embodiment the hybridization affects the translation of a protein from mRNA. In another embodiment of the present disclosure, the hybridization of the multiple CPP-AON conjugate to a micro RNA binding site on a pre-mRNA or mRNA can relieve the target pre-mRNA or mRNA from subsequent regulation by the micro RNA. In this case the effect could be to enhance expression of the gene product encoded by the pre mRNA or mRNA. In contrast, if the multiple CPP-AON, for example, a multiple-CPP PMO, were to be targeted to sequences within the micro RNA such that the biological activity of the microRNA were impeded, the effect would probably be to enhance expression of a variety of gene products under repression by that particular micro RNA.

The overall effect of such interference with a target polynucleotide is selective modulation of the expression of a gene. In the context of the present disclosure, "modulation" means either an increase (stimulation) or a decrease (inhibition) in the expression of a gene.

AONs according to the present disclosure include PMO compounds as well as PNA compounds, phosphoramidate compounds, methylene methylimino ("MMI") compounds, 2-O-methyl compounds and 2-methoxy ethyl compounds, wherein the oligonucleobase of each subunit are set forth in FIG. 1. The oligonucleotide compounds are synthetic analogs of natural nucleic acids. In particular, instead of deoxyribose rings and phosphate-linkages, the oligonucleotide compounds comprise subunits comprised of the respective oligonucleotide subunits shown below:

Formula I

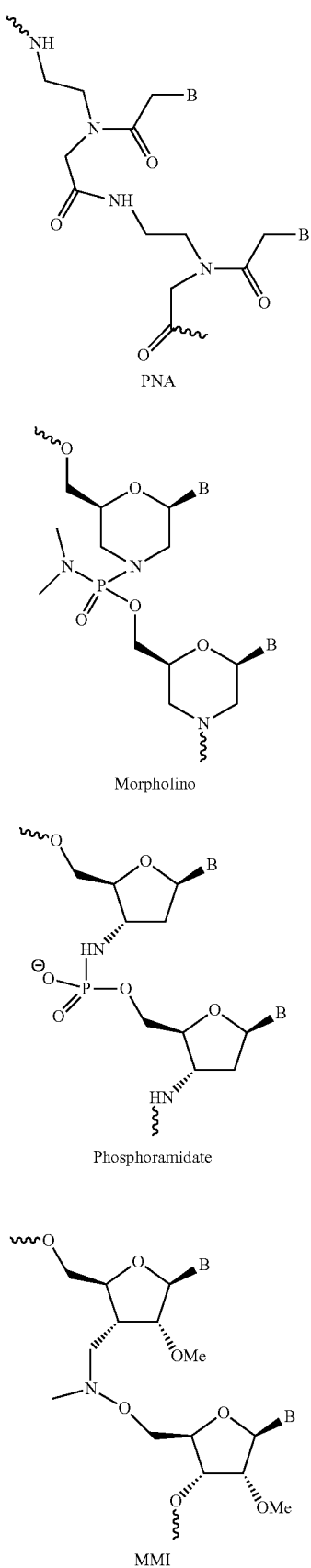

PNA

Morpholino

Phosphoramidate

MMI

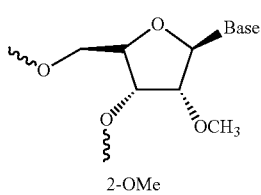

2-OMe

Formula V

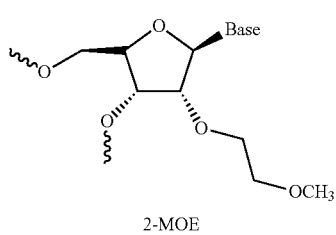

2-MOE

Formula VI

Formula II

Formula III

In the case of each of Formula 1-VI, B is a nucleotide base. The primary nucleobases are cytosine (DNA and RNA), guanine (DNA and RNA), adenine (DNA and RNA), thymine (DNA) and uracil (RNA), abbreviated as C, G, A, T, and U, respectively. A, G, C, and T appear in DNA, these molecules are called DNA-bases; A, G, C, and U are called RNA-bases. Uracil replaces thymine in RNA. These two bases are identical except that uracil lacks the 5' methyl group. Adenine and guanine belong to the double-ringed class of molecules called purines (abbreviated as R). Cytosine, thymine, and uracil are all pyrimidines (abbreviated as Y).

PMO compounds possess subunits comprised of morpholine rings and phosphorodiamidate-linking groups, respectively. For example, the present disclosure includes a PMO compound comprising from 15 to 30 subunits of Formula (II):

Formula IV

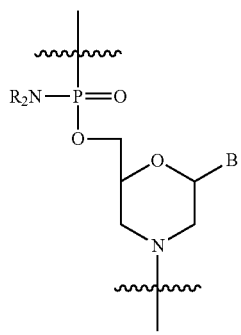

wherein R is an alkyl group and B is a naturally occurring purine or pyrimidine nucleotide base selected from cytosine (C), guanine (G), adenine (A), or thymine (T).

PNA compounds possess subunits comprised of subunits of Formula I. For the present disclosure includes a PMO compound comprising from 15 to 30 subunits of Formula I:

Formula I

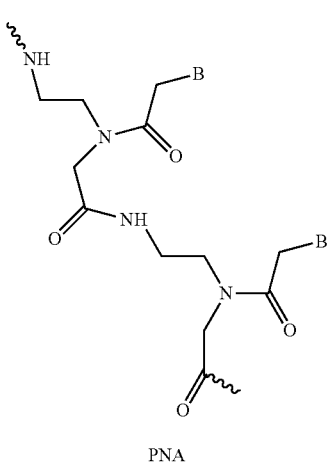

PNA wherein B is a purine or pyrimidine nucleotide base selected from cytosine (C), guanine (G), adenine (A), or thymine (T).

Phosphoramidate compounds possess subunits comprised of subunits of Formula III. For the present disclosure includes a phosphoramidate compound comprising from 15 to 30 subunits of Formula III:

Formula III

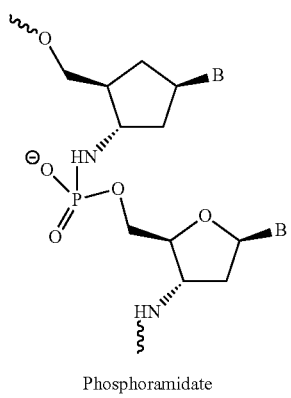

Phosphoramidate wherein B is a purine or pyrimidine nucleotide base selected from cytosine (C), guanine (G), adenine (A), or thymine (T).

MMI compounds possess subunits comprised of the subunits of Formula IV. For example, the present disclosure includes an MMI compound comprising from 15 to 30 subunits of Formula (IV):

Formula IV

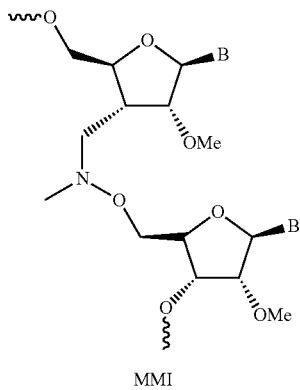

MMI wherein B is a purine or pyrimidine nucleotide base selected from cytosine (C), guanine (G), adenine (A), or thymine (T).

2-OMe compounds possess subunits comprised of Formula V. For example, the present disclosure includes a 2-OMe compound comprising from 15 to 30 subunits of Formula (V):

Formula V

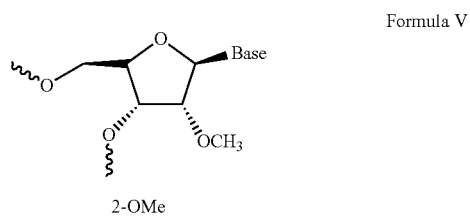

2-OMe wherein B is a purine or pyrimidine nucleotide base selected from cytosine (C), guanine (G), adenine (A), or thymine (T).

2-MOE compounds possess subunits comprised of Formula VI. For example, the present disclosure includes a 2MOE compound comprising from 15 to 30 subunits of Formula (VI):

Formula VI

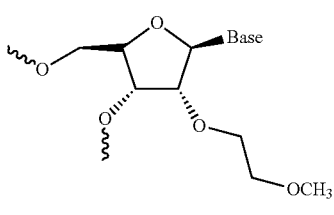

2-MOE wherein B is a purine or pyrimidine nucleotide base selected from cytosine (C), guanine (G), adenine (A), or thymine (T).

The above description of each class of AON can each be substituted where AON-CPP is set forth in the description, e.g. 2MOE-CPP, MMI-CPP, 2-OMe-OPP, PNA-CPP, and Phosphoramidate-CPP.

In at least one embodiment, the AON compound has from 15-25 subunits of formula (I), (II), (III), (IV), (V), or (VI). In another embodiment, the AON compound has from 20-25 subunits of formula (I), (II), (III), (IV), (V), or (VI). In yet another embodiment, the AON compound has about 25 subunits of formula (I), (II), (III), (IV), (V), or (VI), such as from 24-26 subunits.

According to the present disclosure, the multiple PMO-CPP conjugates have less than 60% of PMO subunits where the nucleobase (B) is C or G. In at least one embodiment, the multiple PMO-CPP conjugate has less than 50% of PMO subunits where the nucleobase is C or G.

According to the present disclosure, the multiple AON-CPP conjugates have less than 60% of AON (of formula (I), (II), (III), (IV), (V), or (VI)) subunits where the nucleobase (B) is C or G. In at least one embodiment, the multiple AON-CPP conjugate has less than 50% of AON subunits where the nucleobase is C or G.

The multiple PMO-CPP conjugates of the present disclosure have at least two PMO compounds having from 0 to 3 repeating subunits where the nucleobase is G. In at least one embodiment, the multiple PMO-CPP conjugate has 0 repeating subunits where B is G. In another embodiment the multiple PMO-CPP conjugate has 1, 2, or 3 repeating subunits where B is G. Multiple conjugation sites on the CPP are introduced by adding glutamic acid in the D- or L-enantiomeric position to reduce stearic hindrance of multiple PMOs in close proximity at the termini of the CPP. The use of a peptidase cleavage site with the amino acids Phenylalanine-Lysine at the P1, −P1 positions is introduced between the CPP and the PMO. Cleavage of the peptidase cleavage site releases the PMO from the CPP. For example, the CPP may be attached to the PMO via a maleimide esterized linker with an enzyme cleavage site Phenylalanine-Lysine or Valine-Citruline that could be introduced at a cysteine position. The CPP may be attached by an amide linkage.

The multiple AON-CPP conjugates of the present disclosure have at least two AON compounds having from 0 to 3 repeating subunits where the nucleobase is G. In at least one embodiment, the multiple AON-CPP conjugate has 0 repeating subunits where B is G. In another embodiment the multiple AON-CPP conjugate has 1, 2, or 3 repeating subunits where B is G. Multiple conjugation sites on the CPP are introduced by adding glutamic acid in the D- or L-enantiomeric position to reduce stearic hindrance of multiple AONs in close proximity at the termini of the CPP. The use of a peptidase cleavage site with the amino acids Phenylalanine-Lysine at the P1, −P1 positions is introduced between the CPP and the AON. Cleavage of the peptidase cleavage site releases the AON from the CPP. For example, the CPP may be attached to the AON via a maleimide esterized linker with an enzyme cleavage site Phenylalanine-Lysine or Valine-Citruline that could be introduced at a cysteine position. The CPP may be attached by an amide linkage.

Internalization into the cell using the peptide may result in an intracellular protease, including for example a lysosomal enzyme, cleaving the cleavage site and the free PMO, or AON, would have lower stearic hindrance from the peptide bound conjugate. This lower stearic constraint could increase exon skipping efficiency with less toxicity to the nucleus and cytosol.

According to the present disclosure, the CPP component of the multiple PMO-CPP conjugate can be selected from known CPPs, such as those named A-N, having the sequences in Tables 1, 2, FIG. 1 or the K Series or B series CPPs described herein.

According to the present disclosure, the CPP component of the multiple AON-CPP conjugate can be selected from known CPPs, such as those named A-N, having the sequences in Tables 1, 2, FIG. 1 or the K Series or B series CPPs described herein.

In at least one embodiment the CPP component is peptide K: RXRRXRRXRRXRXB (SEQ ID NO: 43), where R is D-arginine, X is 6-aminohexanoic acid and B is β-alanine. In another embodiment the CPP component is peptide B: RXRRBRRXRRBRXB (SEQ ID NO: 44), wherein R, X, and B are hereinabove defined.

The CPP component of the multiple PMO-CPP, or AON-CPP, conjugates of the present disclosure may also be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl. In some embodiments, the linker is a sequence that contains a cleavage motif. In some embodiments, the cleavage motif can be cleaved by any hydrolytic enzyme. In some embodiments, the cleavage motif can be cleaved by a peptidase or protease such as cathepsin or trypsin. In some embodiments, the linker can be designed to include a cleavage motif recognized by a particular serine protease, threonine protease, cysteine protease, aspartate protease, glutamic acid protease, or metalloprotease, or a group of more than one peptidase. In some embodiments, the linker may include two or more cleavage motifs that are overlapping or nonoverlapping. In some embodiments, the linker may contain no cleavage motifs. In some embodiments, the linker may be designed so that less than 100%, less than 75%, less than 50%, or less than 10% of the linkers are cleaved. In some embodiments, the linker is designed so that greater than 90% or 99% of the linkers are cleaved.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the variable sequence comprises an α-, β-, γ-, or δ-amino acid, or a cycloalkane structure.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the variable sequence causes the compound to be targeted to the nucleus.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the variable sequence causes the compound to be targeted to the cytosol.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the variable sequence causes the compound to be targeted to the mitochondria.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the spacer comprises an aminohexanoic acid (Ahx).

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the spacer comprises (Ahx)B, wherein B is selected from β-alanine or β-glycine.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises a cleavage motif.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; wherein the linker comprises a cleavage motif; and wherein the cleavage motif is cleavable by a hydrolytic enzyme.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FS.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FSQ.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FSQK.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of glutamic acid.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of aspartic acid.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of lysine.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of serine.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of E, D, K, S or T In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the spacer comprises an aminohexanoic acid (Ahx); and wherein the linker comprises FSQG-OH.

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl; and wherein the linker comprises FxyB, x is any amino acid, y is selected from glutamic acid (E), aspartic acid (D), lysine (K), serine (S), and threonine (T), and B is β-alanine; and wherein y is a non-natural analog of threonine; and wherein n is 7, and the spacer is (Ahx).

In some embodiments, the CPP may be a compound comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl, wherein the variable sequence, the spacer, and the linker comprise a sequence selected from: SEQ ID NOs: 1, 2, 3, 4, 5, 6, 7, 8, 9, 10, and 11.

In some embodiments, the CPP-PMO, or CPP-AON, may be a comprising the formula variable sequence-spacer-linker, wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl, further comprising a cargo conjugated to the linker, wherein the cargo comprises a phosphorodiamidate morpholino oligomer (PMO).

In some embodiments, the CPP-PMO, or CPP-AON, may be a compound comprising the formula variable sequence-spacer-linker, wherein the variable sequence is Ac—R(O) nR, wherein n≥7; wherein O is a sequence of residues selected from R, X, and Z; wherein R is L-arginine, X is 3-cis-aminocyclohexane, and Z is cis-2-aminocyclopentane-1-carbonyl, further comprising a cargo conjugated to the linker, wherein the cargo further comprises one or more additional PMOs.

In some embodiments, the CPP may include a variable sequence-spacer-linker according to any of the sequences of Table 1:

TABLE 1

| Hit | Sequence | Local-ization | SEQ ID NO: |
|---|---|---|---|
| 2C4 | Ac-RXXXXXRRR(Ahx)FSQG-OH | Nucleus | 1 |
| 4G9 | Ac-RXXXXXXRR(Ahx)FSQG-OH | Nucleus | 2 |
| 9F5 | Ac-RXXXRXRXR(Ahx)FSQG-OH | Nucleus | 3 |
| 12G4 | Ac-RRXXZXXXR(Ahx)FSQG-OH | Nucleus | 4 |
| 12D10 | Ac-RRRXXXXXR(Ahx)FSQG-OH | Nucleus | 5 |
| 12D11 | Ac-RXRXXXXXR(Ahx)FSQG-OH | Nucleus | 6 |
| 12E4 | Ac-RRZXXXXXR(Ahx)FSQG-OH | Nucleus | 7 |
| 21A5 | Ac-RXXXXZXZR(Ahx)FSQG-OH | Nucleus | 8 |
| 11G1 | Ac-RXXZXRXXR(Ahx)FSQG-OH | Cytosol | 9 |
| 12D4 | Ac-RRXRXXXXR(Ahx)FSQG-OH | Cytosol | 10 |
| 13D2 | Ac-RRZXXZXXR(Ahx)FSQG-OH | Cytosol | 11 |

In some embodiments, the CPP may include the following sequences set forth in Table 2

TABLE 2

| Hit | Sequence | SEQ ID NO: |
|---|---|---|
| 9H8 | Ac-RXXXXXRXR(Ahx) | 12 |
| 9H9 | Ac-RZXXXXRXR(Ahx) | 13 |
| 9H11 | Ac-RXZXXXRXR(Ahx) | 14 |
| 1A2 | Ac-RRRRRRRRR(Ahx) | 15 |
| 12D12 | Ac-RZRXXXXXR(Ahx) | 16 |
| 13D3 | Ac-RXZXXZXXR(Ahx) | 17 |
| 12D10 | Ac-RRRXXXXXR(Ahx) | 18 |
| 2C4 | Ac-RXXXXXRRR(Ahx) | 19 |
| 4G9 | Ac-RXXXXXXRR(Ahx) | 20 |
| 11F4 | Ac-RXXXXRXXR(Ahx) | 21 |
| 9F5 | Ac-RXXXRXRXR(Ahx) | 22 |
| 12D11 | Ac-RXRXXXXXR(Ahx) | 23 |
| 20B7 | Ac-RXXXXXXZR(Ahx) | 24 |
| 20C4 | Ac-RXXZXXXZR(Ahx) | 25 |
| 5D4 | Ac-RXXXRZXRR(Ahx) | 26 |
| 9H7 | Ac-RRXXXXRXR(Ahx) | 27 |
| 5B1 | Ac-RXXXZXXRR(Ahx) | 28 |
| 4H6 | Ac-RXXZXXXRR(Ahx) | 29 |
| 12D4 | Ac-RRXRXXXXR(Ahx) | 30 |
| 15A8 | Ac-RXXXXXZXR(Ahx) | 31 |
| 12D8 | Ac-RXZRXXXXR(Ahx) | 32 |
| 12E3 | Ac-RZXXXXXXR(Ahx) | 33 |
| 12H2 | Ac-RXXZZXXXR(Ahx) | 34 |
| 4G10 | Ac-RZXXXXXRR(Ahx) | 35 |
| 15H5 | Ac-RXXXXZZXR(Ahx) | 36 |
| 11F1 | Ac-RXRXXRXXR(Ahx) | 37 |
| 21C7 | Ac-RRXXZZXZR(Ahx) | 38 |
| 12E2 | Ac-RXXXXXXXR(Ahx) | 39 |
| 12E4 | Ac-RRZXXXXXR(Ahx) | 40 |
| 12G4 | Ac-RRXXZXXXR(Ahx) | 41 |
| 21A5 | Ac-RXXXXZXZR(Ahx) | 42 |

One of ordinary skill in the art will be able to design additional CPP sequences that will achieve the goals of the present disclosure, such as enhanced cellular penetration. As a result, the presently disclosed multiple PMO-CPP and AON-CPP conjugates are not limited to the CPP components disclosed herein.

As used herein, NOAEL means the dosage level where no untoward effects are observed. In other words, the NOAEL is the maximum safe dose.

In some embodiments, the linker is a sequence that contains a cleavage motif. In some embodiments, the cleavage motif can be cleaved by any hydrolytic enzyme. In some embodiments, the cleavage motif can be cleaved by a peptidase or protease such as cathepsin or trypsin. As used herein, cathepsin cleavable linker is synonymous with cathepsin cleavage site. The cleavable linker according to the present disclosure is capable of being cleaved, i.e., chemically degraded, by intracellular enzymes. In some embodiments, the linker can be designed to include a cleavage motif recognized by a particular serine protease, threonine protease, cysteine protease, aspartate protease, glutamic acid protease, or metalloprotease, or a group of more than one peptidase. In some embodiments, the linker may include two or more cleavage motifs that are overlapping or nonoverlapping. In some embodiments, the linker may contain no cleavage motifs. In some embodiments, the linker may be designed so that less than 100%, less than 75%, less than 50%, or less than 10% of the linkers are cleaved. In some embodiments, the linker is designed so that greater than 90% or 99% of the linkers are cleaved.

In some embodiments, the linker includes the sequence FS (SEQ ID NO.:45). In some embodiments, the linker includes the sequence FSQ (SEQ ID NO.: 46) or FSQK (SEQ ID NO.:47). In some embodiments, the linker includes the sequence FxyB (SEQ ID NO.: 48), where x is any amino acid, standard or nonstandard, y is glutamic acid (E), aspartic acid (D), and lysine (K), serine (S), or threonine (T), and B is β-alanine or β-glycine. In some embodiments, suitable cathepsin cleavage sites include FKE (SEQ ID NO.: 49), FAE (SEQ ID NO.: 50), FVE (SEQ ID NO.: 51), FLE (SEQ ID NO.: 52), FSE (SEQ ID NO.: 53), and V[Cit]E (SEQ ID NO.: 54), wherein F is phenylalanine, K is lysine, E is glutamic acid, A is alanine, V is valine, L is leucine, S is serine, and Cit is citruline. The present disclosure is not limited to the specific cathepsin linkers disclosed herein, but also include additional amino acid sequences capable of being cleaved by intracellular proteases.

EXAMPLES

Peptide Synthesis

Peptides were synthesized using a Ranin Symphony automated peptide synthesizer using standard Fmoc-chemistry on pre-loaded CLEAR (Cross-Linked Ethoxylate Acrylate Resin) (Peptides International, Louisville, Ky.). Amino acids (EMD Biosciences, San Diego, Calif. or Anaspec, San Jose, Calif.) were orthogonally protected with tert-butoxycarbonyl (BOC), tert-butyl (tBu) 2,2,4,6,7-pentamethyldihydrobenzofuran-5-sulfonyl (Pbf), or Trityl (Trt) groups. Couplings were performed using an amino acid/HCTU/N-Methylmorpholine/resin molar ration of 5/5/10/1. 20% piperidine, 2% 1,8-diazabicyclo[5.4.0]-undec-7-ene (DBU) in DMF was used to remove Fmoc from the amine terminus during each cycle. N-terminal acetylation was performed on resin using acetic anhydride/NMM/resin in DMF in a molar ratio of 30/8/1. Deprotection/cleavage from resin was performed using a mixture of 15 ml/0.1 mM resin of 2.5% water/2.5% TIS/5% Anisole/90% TFA v/v ratio for 3 hr. Supernatant was precipitated in diethylether (−80° C.) and pelleted at 3000 rpm for 10 min. Ether was decanted and pellet was washed again. Crude peptide was lyophilized and purified using semi-preparative reversed-phase HPLC (XBridge C18, 10×250 mm, 5 µm particle size). Purification was performed at 5 ml/min with a load gradient of 99% Buffer-A (water, 0.1% TFA) and 1% Buffer-B (Acetonitrile, 0.1% TFA) (gradient slope, 0.3% B/min). Peptide purity >95% was evaluated by reversed-phase analytical HPLC and MALDI-TOF (Waters Synapt). Fractions were pooled, lyophilized, and redissolved in appropriate conjugation buffers. (All solvents were of HPLC grade purchased from EMD Biosciences, San Diego, Ca or Sigma Aldrich, St. Louis, Mo.)

Peptide (CPP)-PMO Conjugation

PMOs were ordered with a 5'-end primary amine and peptides were synthesized as described above. In single PMO-CPP conjugates, peptide was used in 2-fold molar excess compared to PMO, and in multiple PMO-CPP conjugates, moles of PMOs were calculated using the following equation: (1.2-fold)×(Number of Conjugates)×(moles of peptide). The PMOs were dissolved in DMSO (5 mM) and set aside. Peptides were dissolved in DMF (50 mM) and mixed with a molar equivalent of the aminium-based coupling reagent 2-(6-chloro-1-H-benzotriazole-1-yl)-1,1,3,3-tetramethylaminium hexafluorophosphate. 4-Methylmorpholine (NMM) at 2 molar equivalents was added to the peptide mixture and immediately added to the PMO solution. Reaction proceeded for 1.5 hr at 37° C. and was stopped using 4 volume equivalents of water. The mixture was added to a CM sepharose (Sigma Aldrich, St. Louis, Mo.) column and washed with 10 column volumes to remove unconjugated PMO and reactants. Peptide CPP-PMO conjugates were eluted from the column with 1M guanidium-HCL, 1M NaCl and dialyzed against 100 mM $NH_4HCO_3$ with 3 buffer exchanges to remove salts and unconjugated peptide. Dialyzed material was lyophilized and analyzed with analytical HPLC.

The following CPPs were synthesized according to the general peptide synthesis protocol described above:

No. 1215:
(SEQ ID NO.: 55)
Ac-(RXRRBR)$_2$XFKEG-OH

No. 1216:
(SEQ ID NO.: 56)
Ac-(RXRRBR)$_2$XFD(d-Glu)EG-OH

No. 1217:
(SEQ ID NO.: 57)
Ac-E(RXRRBR)$_2$XFKG-amide

No. 1218:
(SEQ ID NO.: 58)
Ac-E(RXRRBR)$_2$XFKG-OH

No. 1219:
(SEQ ID NO.: 59)
Ac-E(RXRRBR)$_2$XFKEG-OH

No. 1220:
(SEQ ID NO.: 60)
Ac-E(RXRRBR)$_2$XFK(d-Glu)EG-OH

No. 1221:
(SEQ ID NO.: 61)
Ac-(d-Glu)E(RXRRBR)$_2$xFKG-amide

No. 1222:
(SEQ ID NO.: 62)
Ac-(dGlu)E(RXRRBR)$_2$XFKG-OH

No. 1223:
(SEQ ID NO.: 63)
Ac-(d-Glu)E(RXRRBR)$_2$XFKEG-OH

No. 1224:
(SEQ ID NO.: 64)
Ac-(d-Glu)E(RXRRBR)$_2$XFK((d-Glu)EG-OH

No. 1225-B:
(SEQ ID NO.: 65)
Biot-(RXRRBR)$_2$XFKG-OH

No. 1225-F:
(SEQ ID NO.: 66)
FITC-(RXRRBR)$_2$XFKG-OH

No. 1226-B:
(SEQ ID NO.: 67)
Ac-(RXRRBR)$_2$XFK(Biot)G-OH

No. 1226-F:
(SEQ ID NO.: 68)
Ac-(RXRRBR)$_2$XFK(FITC)G-OH wherein Ac is acetyl, R is D-arginine, X is 6-aminohexanoic acid, B is β-alanine, FK is a cathepsin cleavage site, E is glutamic acid, G is glycine, Biot is biotin, and FITC is fluorescein isothiocyanate.

The CPPs listed above were conjugated with PMO23 to form PMO-CPP conjugates using the synthesis procedure described above. The conjugates formed according to this procedure had the following sequences:

No. 1215:
Ac-(RXRRBR)₂XFKE(PMO)G(PMO) (SEQ ID NO.: 69)

No. 1216:
Ac-(RXRRBR)₂XFD(d-Glu)(PMO)E(PMO)G(PMO) (SEQ ID NO.: 70)

No. 1217:
Ac-E(PMO)(RXRRBR)₂XFKG (SEQ ID NO.: 71)

No. 1218:
Ac-E(PMO)(RXRRBR)₂XFKG(PMO) (SEQ ID NO.: 72)

No. 1219:
Ac-E(PMO)(RXRRBR)₂XFKE(PMO)G(PMO) (SEQ ID NO.: 73)

No. 1220:
Ac-E(PMO)(RXRRBR)₂XFK(d-Glu)(PMO)E(PMO)G(PMO) (SEQ ID NO.: 74)

No. 1221:
Ac-(d-Glu)(PMO)E(PMO)(RXRRBR)₂XFKG (SEQ ID NO.: 75)

No. 1222:
Ac-(dGlu)(PMO)E(PMO)(RXRRBR)₂XFKG(PMO) (SEQ ID NO.: 76)

No. 1223:
Ac-(d-Glu)(PMO)E(PMO)(RXRRBR)₂XFKE(PMO)G(PMO) (SEQ ID NO.: 77)

No. 1224:
Ac-(d-Glu)(PMO)E(PMO)(RXRRBR)₂XFK(d-Glu)(PMO)E(PMO)G(PMO) (SEQ ID NO.: 78)

No. 1225-B:
Biot-(RXRRBR)₂XFKG(PMO) (SEQ ID NO.: 79)

No. 1226-B:
Ac-(RXRRBR)₂XFK(Biot)G(PMO) (SEQ ID NO.: 80)

The above-referenced CPP-PMO conjugates as well as No. 1120 (Ac—(RXR)₄XFKE-((PEG)₂-PMO)G-(PMO)) (SEQ ID NO.: 81) and (Ac—(RXRRBR)₂XBA-PMO) (SEQ ID NO.: 82) were administered intravenously to wild-type mice at a dose of 2.84 µM/kg.

Following the end of dosing, tissue was harvested under anesthesia and frozen in liquid nitrogen. Frozen heart and quadriceps were processed to isolate RNA. Samples were quantified using a nanodrop ND1000 spectrophotometer. Samples were further diluted to a concentration of 15 ng/µl. Samples were amplified using primers having the following sequences: CAGAATTCTGCCAATTGCTGAG (SEQ ID NO.: 83) and TTCTTCAGCTTGTGTCATCC (SEQ ID NO.: 84). PCR was conducted with a run sequence of 55° C./30 min.; 94° C./2 min; 94° C./15 s×30 times; 55° C./30 s; 68° C./1.5 min.

The percentage of exon 23 skipping for each conjugate is shown in Table 3.

TABLE 3

| Conjugate | % Exon 23 Skipping (mean) | |
|---|---|---|
| | Quadricep | Heart |
| PBS Buffer (control) | 0 | 0 |
| 1120 | 48.7 | 1.3 |
| 1204 | 75.7 | 33.7 |
| 1215 | 25.5 | 0.8 |
| 1216 | 69.5 | 28.5 |
| 1217 | 0 | 0 |
| 1218 | 4.3 | 0 |
| 1219 | 36.5 | 0.8 |
| 1220 | 10.7 | 0.7 |
| 1221 | 11.3 | 5 |
| 1222 | 9.5 | 0 |
| 1223 | 40 | 0 |
| 1224 | 15 | 0 |
| 1225-B | 66.7 | 6.7 |
| 1226-B | 39 | 1.2 |

PMOs conjugated to the N-terminus of the CPP did not perform as well as the same number of PMOs conjugated to the C-terminus. Conjugate No. 1212 did not perform as well as the K-peptide conjugate No. 1120. No. 1204, with only one PMO, performed better than conjugate No. 1120, with two PMOs. No. 1225-B performed better than No. 1226-B.

The following additional CPP-PMO conjugates were synthesized according to the above procedures. The PMO used for the conjugates below is GGCCAAACCTCGGCTTACCTGAAAT (SEQ ID NO.: 85).

K Series (PMO is PMO23):

No. 1118:
Ac-(RXR)₄XEG-(PMO) (SEQ ID NO.: 86)

No. 1119:
Ac-(RXR)₄XE-((PEG)₂-PMO)G-(PMO) (SEQ ID NO.: 87)

No. 1120:
Ac-(RXR)₄XFKE-((PEG)₂-PMO)G-(PMO) (SEQ ID NO.: 81)

No. 970-S:
Stearyl-(RXR)₄XA-PMO (SEQ ID NO.: 88)

B Series (PMO is PMO23):
No. 1204:
Ac-(RXRRBR)₂XBA-PMO (SEQ ID NO.: 82)

E(PMO)(RXRRBR)₂XFKG, "n-terminal PPMO-B" (SEQ ID NO.: 89)

No. 1239:
Ac-(RXRRBR)₂XE(PMO)G(PMO) (SEQ ID NO.: 90)

Ac-(RXRRBR)₂FKEG-(PMO)₂, "Di-PMO-B + FK" (SEQ ID NO.: 91)

wherein Ac is acetyl, R is D-arginine, X is 6-aminohexanoic acid, B is β-alanine, FK is a cathepsin cleavage site, E is glutamic acid, and G is glycine.

In some embodiments, X can also include other types of residues, such as proline, glycine, or alanine, or additional modified or nonstandard amino acids. In some embodiments, the variable sequence includes alpha, beta, gamma, or delta amino acids, or cycloalkane structures. In some embodiments, the linker includes the sequence FS (SEQ ID NO.: 45). In some embodiments, the linker includes the sequence FSQ (SEQ ID NO.: 46) or FSQK (SEQ ID NO.: 47), wherein F is phenylanine, S is serine, K is lysine and Q is glutamine. In some embodiments, the linker includes the sequence FxyB (SEQ ID NO.: 48), where x is any amino acid, standard or nonstandard, y is glutamic acid (E), aspartic acid (D), and lysine (K), serine (S), or threonine (T), and B is β-alanine or β-glycine Wild-type mice were intravenously administered conjugate Nos. 1204, 1119, 1120, 1239, and 1215 at a dose of 2.84 μM/kg. Tissues were harvested and RNA was isolated as described above. The percentage of exon 23 skipped is shown in Table 4.

TABLE 4

| | % Exon 23 Skipping (mean) | |
|---|---|---|
| Conjugate | Quadricep | Heart |
| PBS Buffer (control) | 0 | 0 |
| 1204 | 54.3 | 0 |
| 1119 | 44.9 | 0.4 |
| 1120 | 68 | 16.6 |
| 1239 | 2.6 | 0 |
| 1215 | 21.3 | 0 |

Figure 3:
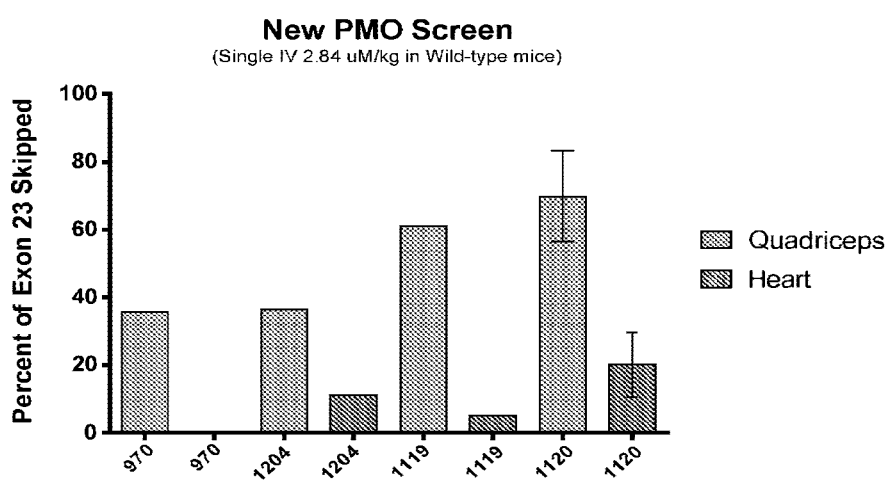
FIG. 3 is depicts the effects of some of the CPP-PMO conjugates on exon 23 skipping in wild-type mice.

FIG. 3 also depicts the effects of some of the multiple CPP-PMO conjugates on exon 23 skipping in wild-type mice.

As shown above, efficacy was improved by attaching more than one PMO to a single CPP-K but not CPP-B. A single dose of CPP-B delivered by IV injection, conjugated to 2 PMO exon 23 moieties (No. 1239) was far less effective than CPP-B conjugated to a single PMO exon 23 (No. 1204). Surprisingly, we found that a single dose of CPP-K conjugated to 2 PMOs (No. 1119) in exactly the same chemical fashion was roughly two times as efficacious as a single dose of CPP-K conjugated to a single PMO exon 23 (No. 1118). Interestingly, CPP-PMO23B was more efficacious than CPP-PMO23K as a monomeric construct. In multiple CPP-PMO conjugate studies where three PMOs were tethered to a CPP, three PMO23 moieties conjugated to a single peptide B (No. 1216) doubled the activity compared to the di-PMO B (although tri-PMO23-B was similar to di-PMO23-K in terms of its exon skipping capacity). These results suggest that it cannot be predicted a priori which multiple CPP-PMO conjugate will have the desired properties, and therefore, one of ordinary skill in the art will have to conduct preliminary studies using the methods described in the present disclosure to determine the efficacy for each conjugate prepared.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A peptide-antisense oligonucleotide (peptide-AON) conjugate comprising a polycationic peptide covalently conjugated to at least two antisense oligonucleotides (AONs), wherein each AON comprises:
   (a) 15 to 30 subunits of a phosphorodiamidate morpholino (PMO),
      wherein each subunit comprises a naturally occurring purine or pyrimidine nucleotide base selected from the group consisting of C, G, A, and T;
   (b) a nucleotide base sequence that is complementary to at least 8 contiguous bases of a target pre-mRNA, mRNA, microRNA, or long non-coding RNA of a gene;
   (c) from 0 to 3 repeating subunits where the naturally occurring purine nucleotide base is G;
   (d) less than 60% of said subunits where the naturally occurring purine or pyrimidine nucleotide base is C or G; and
   (e) a non-self-complimentary sequence;
   wherein the polycationic peptide is a cationic cell penetrating peptide (CPP), and wherein the peptide-AON conjugate comprises a cleavable linker containing a cleavage motif.

2. The peptide-AON conjugate of claim 1, wherein the cleavable linker comprises FK or FX at the P1/P1' position, where X is any naturally occurring amino acid.

3. The peptide-AON conjugate of claim 1, wherein the cleavage motif is a hydrolytic enzyme cleavage motif.

4. The peptide-AON conjugate of claim 1, wherein the CPP comprises:
   (a) RXRRXRRXRRXRXB (SEQ ID NO: 43),
      where R is D-arginine, X is 6-aminohexanoic acid, and B is β-alanine; or
   (b) RXRRBRRXRRBRXB (SEQ ID NO: 44),
      wherein R is D-arginine, X is 6-aminohexanoic acid, and B is β-alanine.

5. The peptide-AON conjugate of claim 1, wherein the CPP comprises the formula: variable sequence-spacer-linker,
   wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl, and
   wherein the variable sequence:
      (i) comprises an α-, β-, γ-, or δ-amino acid, or a cycloalkane structure;

(ii) causes the compound to be targeted to the nucleus;
(iii) causes the compound to be targeted to the cytosol; or
(iv) causes the compound to be targeted to the mitochondria.

6. The peptide-AON conjugate of claim 1, wherein the polycationic peptide comprises the formula: variable sequence-spacer-linker,
wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl, and
wherein the spacer:
(i) comprises an aminohexanoic acid (Ahx); or
(ii) comprises (Ahx)B, wherein B is selected from β-alanine or β-glycine.

7. The peptide-AON conjugate of claim 1, wherein the polycationic peptide comprises the formula variable sequence-spacer-linker,
wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl, and
wherein the linker:
(i) comprises the sequence FS;
(ii) comprises the sequence FSQ;
(iii) comprises the sequence FSQK; or
(iv) comprises the sequence FxyB, wherein F is phenylalanine, x is any amino acid and y is selected from glutamic acid (E), aspartic acid (D), lysine (K), serine (S), and threonine (T) or a non-natural analog of E, D, K, S or T, and B is β-alanine.

8. The peptide-AON conjugate of claim 1, wherein the CPP comprises the formula: variable sequence-spacer-linker,
wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl,
wherein the spacer comprises an aminohexanoic acid (Ahx) and
wherein the linker comprises FSQG-OH.

9. The peptide-AON conjugate of claim 1, wherein the CPP comprises the formula: variable sequence-spacer-linker,
wherein the variable sequence is Ac—R(O)nR, wherein n≥7; wherein O is a sequence of residues selected from R, X, and Z; wherein R is L-arginine, X is 3-cis-aminocyclohexane, and Z is cis-2-aminocyclopentane-1-carbonyl,
wherein the linker comprises the sequence FxyB, wherein F is phenylalanine, x is any amino acid and y is selected from glutamic acid (E), aspartic acid (D), lysine (K), serine (S), and threonine (T), and B is β-alanine; and wherein y is a non-natural analog of threonine; and wherein n is 7, and
wherein the spacer is (Ahx).

10. The peptide-AON conjugate of claim 1, wherein the CPP comprises a sequence selected from the group consisting of: SEQ ID NOs. 1, 2, 3, 4, 5, 6, 7, 8, 9, 10, and 11.

11. The peptide-AON conjugate of claim 1, wherein the CPP is selected from the group consisting of:

(i) No. 1216:
(SEQ ID NO.: 56)
Ac-(RXRRBR)₂XFD(d-Glu)EG-OH;

(ii) No. 1218:
(SEQ ID NO.: 58)
Ac-E(RXRRBR)₂XFKG-OH;

(iii) No. 1219:
(SEQ ID NO.: 59)
Ac-E(RXRRBR)₂XFKEG-OH;

(iv) No. 1220:
(SEQ ID NO.: 60)
Ac-E(RXRRBR)₂XFK(d-Glu)EG-OH;

(v) No. 1221:
(SEQ ID NO.: 61)
Ac-(d-Glu)E(RXRRBR)₂XFKG-amide (vi) No. 1222:
(SEQ ID NO.: 62)
Ac-(dGlu)E(RXRRBR)₂XFKG-OH;

(vii) No. 1223:
(SEQ ID NO.: 63)
Ac-(d-Glu)E(RXRRBR)₂XFKEG-OH; or (viii) No. 1224:
(SEQ ID NO.: 64)
Ac-(d-Glu)E(RXRRBR)₂XFK((d-Glu)EG-OH, wherein Ac is acetyl, R is D-arginine, X is 6-aminohexanoic acid, B is β-alanine, F is phenylalanine, K is lysine, D is aspartic acid, E is glutamic acid, and G is glycine.

12. The peptide-AON conjugate of claim 1, wherein the peptide-AON conjugate is selected from the group consisting of:
(i) Ac-(RXR)₄XFKE-((PEG)₂-PMO)G-(PMO) (SEQ ID NO:81);
(ii) Ac-(RXRRBR)₂XFD(d-Glu)(PMO)E(PMO)G(PMO) (SEQ ID NO:70);
(iii) Ac-E(PMO)(RXRRBR)₂XFKG (SEQ ID NO:72);
(iv) Ac-E(PMO)(RXRRBR)₂XFKE(PMO)G(PMO) (SEQ ID NO:73);
(v) Ac-E(PMO)(RXRRBR)₂XFK(d-Glu)(PMO)E(PMO)G(PMO) (SEQ ID NO:74);
(vi) Ac-(d-Glu)(PMO)E(PMO)(RXRRBR)₂XFKG (SEQ ID NO:75);
(vii) Ac-(d-Glu)(PMO)E(PMO)(RXRRBR)₂XFKG(PMO) (SEQ ID NO:76);
(viii) Ac-(d-Glu)(PMO)E(PMO)(RXRRBR)₂XFKE(PMO)G(PMO) (SEQ ID NO:77);
(ix) Ac-(d-Glu)(PMO)E(PMO)(RXRRBR)₂XFK((d-Glu)(PMO)E(PMO)G(PMO) (SEQ ID NO:78);
(x) Ac-(RXRRBR)₂XFKE(PMO)G(PMO) (SEQ ID NO:69);
(xi) Ac-(RXR)₄XE((PEG)₂-PMO)G(PMO) (SEQ ID NO:87); and
(xii) Ac-(RXRRBR)₂XE(PMO)G(PMO) (SEQ ID NO:90),
where Ac is acetyl, R is D-arginine, X is 6-aminohexanoic acid, B is β-alanine, F is phenylalanine, K is lysine, D is aspartic acid, E is glutamic acid, and G is glycine.

13. The peptide-AON conjugate of claim 12, wherein the PMO is PMO23.

14. The peptide-AON conjugate of claim 1, wherein the PMO subunit is of Formula (I):
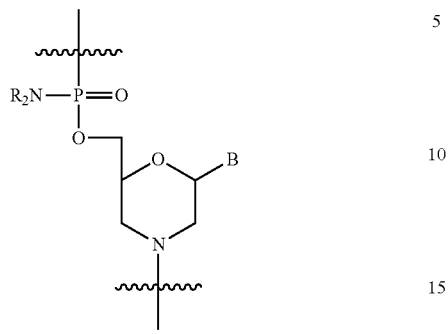
where R is an alkyl group and B is a naturally occurring purine or pyrimidine nucleotide base selected from cytosine (C), guanine (G), adenine (A), or thymine (T).
* * * * *